United States Patent [19]

Bončič

[11] Patent Number: 4,740,372

[45] Date of Patent: Apr. 26, 1988

[54] COMPOSITION FOR TREATING PSORIASIS VULGARIS AND A METHOD FOR ITS PREPARATION

[76] Inventor: Ljubomir Bončič, 11 Oktobar St. No. 7, 18310 Bela Palanka, Yugoslavia

[21] Appl. No.: 908,369

[22] Filed: Sep. 17, 1986

[51] Int. Cl.$^4$ ..................... A61K 31/56; A61K 37/48
[52] U.S. Cl. ................... 424/94.64; 514/170; 514/863
[58] Field of Search ............. 514/170, 180, 39; 424/94

[56] References Cited

U.S. PATENT DOCUMENTS 3,787,454  1/1974  Kerb et al. ................. 514/863 X
3,934,013  1/1976  Poulsen ...................... 514/170

Primary Examiner—Leonard Schenkman
Attorney, Agent, or Firm—Marmorek, Guttman & Rubenstein

[57] ABSTRACT

A composition for the treatment of psoriasis vulgaris, and a method for its preparation are described. The compound is made from the following ingredients: $6\alpha,9\alpha$-difluoro-$11\beta$, $17\alpha$-dihidroxy-$16\alpha$-methyl-21 trimethyl-acetoxy-1,4-pregnadiene-3,20 dione; (+)-17,21-dipropionyloxy-$16\beta$-methyl-$9\alpha$-fluoro-prednisolone; salicylic acid; tetracycline chloride; gentamycin sulfate; neomycin sulfate; trypsin; chymotrypsin; and bismuth. A method for the preparations of this composition is also disclosed. In this method, $6\alpha,9\alpha$-difluoro-$11\beta,17\alpha$-dihidroxy-$16\alpha$-methyl-21-trimethyl-acetoxy-1,4-pregnadiene-3,20 dione and (+)-17,21-dipropionyloxy-$16\beta$-methyl-$9\alpha$-fluoroprednisolone are first mixed together under intensive agitation. Salicyclic acid, tetracycline chloride, gentamycin sulfate and neomycin sulfate are then added. Next, trypsin, chymotrypsin and bismuth are added. Finally, the preparation is mixed into a neutral cream, ointment, etc., at which time it is ready for use. This unique composition of ingredients acting together achieves excellant results in the treatment psoriasis vulgaris.

13 Claims, No Drawings

COMPOSITION FOR TREATING PSORIASIS VULGARIS AND A METHOD FOR ITS PREPARATION

BACKGROUND OF THE INVENTION

This invention relates to a pharmaceutical composition for the treatment of psoriasis vulgaris.

Psoriasis is characterized by pink or red lesions which are covered with silvery scales. These lesions are often found in the folds of the elbows and knees, the scalp and the genitoanal area. The condition is marked by accelerated turnover of the epidermal layer of the skin and consequential epidermal thickness. Psoriasis vulgaris is the common form of the disease.

While normal epidermal turnover occurs every 25-30 days, in psoriatic skin it occurs approximately every 3-4 days. At this rate, the skin color is often affected, resulting in too much or too little pigmentation.

The duration of psoriasis vulgaris is variable. Psoriatic lesions may last a lifetime, or they may disappear within a short period of time.

Many attempts have been made in the past to cure psoriasis vulgaris. The first attempts to treat this condition were through topical agents containing a variety of active ingredients. One of the more popular of these topical agents is an ointment containing salicylic acid as the active ingredient. However, because salicylic acid is an irritant, its use has sometimes resulted in a worsening of the condition.

Another popular active ingredient of the topical agents has been corticosteriods such as hydrocortisone. The corticosteriods have significant suppressive activity which affects psoriasis. However, they also have many untoward effects, such as local atrophy and systemic absorption. There is also a danger of relapse upon discontinuance of use.

In a different approach, exposure to ultraviolet light has been tried, but has met with limited success. Combination therapy of ultraviolet light and coal tar preparations appear to be more effective than the ultraviolet light alone. However, some patients incur a worsening of their condition upon the application of coal tar to affected areas.

More recently, the oral administration of the corticosteriods has shown significant suppressive activity on psoriasis. This course of treatment has considerable drawbacks, including the usual systemic side effects. Moreover, the condition often becomes worse than it was initially upon the cessation of this therapy. For this reason, the systemic use of the corticosteriods is limited to the most severe forms of psoriasis only.

Other systemic treatments which have been tried include cytostatic therapy and Vitamin A and C treatments. The consensus is that these treatments are of questionable value.

All in all, the treatments for psoriasis vulgaris which have been proposed have not been successful. These prior art treatments are either ineffective or accompanied by untoward side effects.

It is therefore an object of the present invention to overcome the deficiencies of the prior art by providing a new composition for the treatment of psoriasis vulgaris in humans and a method for its preparation.

A particular object of the invention is the identification of a mixture which has a unique combination of ingredients which are particularly advantageous in treating the skin areas afflicted with psoriasis vulgaris.

It is a further object of the invention to provide a composition which is effective in the treatment of psoriasis vulgaris and which does not produce harmful side effects.

SUMMARY AND DETAILED DESCRIPTION OF PREFERRED EMBODIMENTS

These and other objects are accomplished by providing a composition which is useful for the treatment of psoriasis vulgaris comprising therapeutically effective amount of the following ingredients:

6$\alpha$,9$\alpha$-difluoro-11$\beta$,17$\alpha$-dihidroxy-16$\alpha$-methyl-21-trimethyl-acetoxy-1,4-pregnadiene-3,20 dione;

(+)-17,21-dipropionyloxy-16$\beta$-methyl-9$\alpha$-fluoro-prednisolone;

salicylic acid;

tetracycline chloride;

gentamycin sulfate;

neomycin sulfate;

trypsin;

chymotrypsin; and bismuth.

The composition containing these ingredients is combined with an ointment or a cream so that it can be applied topically to affected areas of the skin.

The first two compounds mentioned above are members of the corticosteroid class of drugs. In terms of comparative activity to others of their class, they exhibit a mild anti-inflammatory activity. They also relieve itching and constrict local blood vessel actions when applied topically. Because of their mild activity, their untoward effects are not as great as other preparations in the prior art.

Salicylic acid, when applied topically, removes the upper skin layers without affecting the structure of the viable epidermis below.

Tetracycline chloride, gentamycin sulfate, and neomycin sulfate are all well-known antibiotics which, when used topically together, exhibit a wide range of activity. Tetracycline itself possesses a wide range of antimicrobial activity against gram-negative and gram-positive bacteria, overlapping that of many other antimicrobial drugs. Likewise, neomycin is also a broad spectrum antibiotic widely used for topical application in a variety of infections. Gentamycin possesses activity against gram-negative bacteria.

Trypsin and chymotryspin are both proteolytic enzymes which act locally upon topical application as debriding agents. Their potency is measured in proteolytic activity and is expressed in armour units.

Bismuth which is used as a dusting powder, is inert and insoluble. It covers and protects the affected epithelial surfaces to prevent friction. It may be omitted from the composition of the present invention if desired.

The composition is prepared by mixing 6$\alpha$,9$\alpha$-difluoro-11$\beta$,17$\alpha$-dihidroxy-16$\alpha$-methyl-21-trimethyl-acetoxy-1,4-pregnadiene-3,20-dione with (+)-17,21-dipropionyloxy-16$\beta$-methyl-9$\alpha$-fluoro-prednisolone as starting materials. Thereafter, salicylic acid, tetracycline chloride, gentamycin sulfate, and neomycin sulfate are added to the starting materials. Finally, trypsin, chymotrypsin and bismuth are added. The ingredients are agitated to attain consistency. Once this is achieved, this preparation is mixed into a neutral base such as a cream or ointment.

The following examples illustrate preferred embodiments of the invention.

EXAMPLE 1

A composition in accordance with the present invention is prepared by intensively agitating 6α,9α-difluoro-11β,17α-dihidroxy-16α-methyl-21-trimethyl-acetoxy-1,4-pregnadiene-3,20-dione with (+)-17,21-dipropionyloxy-16β-methyl-9α-fluoro-prednisolone at a temperature within the range of 25°–30° C., and at an atmospheric pressure of 980 millibar for approximately 10 minutes, after which the composition is allowed to stand for 5–6 hours under the same conditions. Thereafter, the temperature is lowered to about 5°–7° C. and the air humidity is lowered to 30% without changing the atmospheric pressure. Then, the salicylic acid, tetracycline chloride, gentamycin sulfate, and neomycin sulfate are added to the composition and the mixture is intensively agitated for 10–15 minutes. After the agitation period has ended, trypsin, chymotrypsin and bismuth are added. The agitation is continued for an additional 5 minutes at this time. The preparation is then left standing for 24 to 48 hours at a temperature of about 2°–4° C. Finally, one or more inert adjuvants are added. The composition is then ready for use.

EXAMPLE 2

A composition is prepared in accordance with the steps disclosed in Example 1, which composition contains the following:

| INGREDIENT | AMOUNT |
|---|---|
| 6α,9α-difluoro-11β,17α-dihidroxy-16α-methyl-21-trimethyl-acetoxy-1,4-pregnadiene-3,20-dione | 6–12 mg. |
| (+)-17,21-dipropionyloxy-16β-methyl-9α-fluoro-prednisolone | 20–25 mg. |
| salicylic acid | 3–10 g. |
| tetracycline chloride | 9–14 g. |
| gentamycin sulfate | 45 mg. (i.u. %) |
| neomycin sulfate | 200–250 mg. |
| trypsin | 5000 armour units |
| chymotrypsin | 5000 armour units |
| bismuth | 0–4 g. |
| adjuvants | sufficient to make 100 g |

EXAMPLE 3

A composition is prepared in accordance with the steps disclosed om Example 1, which composition contains the following:

| INGREDIENT | AMOUNT (in atomic %) |
|---|---|
| 6α,9α-difluoro-11β,17α-dihidroxy-16α-methyl-21-trimethyl-acetoxy-1,4-pregnadiene-3,20 dione | 0.22% |
| (+)-17,21-dipropionyloxy-16β-methyl-9α-fluoro-prednisolone | 0.9% |
| salicyclic acid | 20% |
| tetracycline chloride | 62% |
| gentamycin sulfate | minimum 45 i.u. |
| neomycin sulfate | 9% |
| trypsin | 5000 armour units |
| chymotrypsin | 5000 armour units |
| bismuth | 6.6% |
| neutral cream or ointment | 44 g. |

The unique combination of ingredients disclosed herein act in tandem to achieve unexpected results making this invention particularly efective in the treatment of psoriasis vulgaris. The preparations show activity about 24–48 hours after the first application. Impressive therapeutic results are achieved after 15 to 20 days of treatment.

Whereas preferred embodiments of the present invention have been described above for purposes of illustration, it will be apparent to those skilled in the art that certain variations of the details may be made without departing from the spirit or scope of the invention.

What is claimed is:

1. A composition useful for the treatment of psoriasis vulgaris comprising therapeutically effective amounts of the following ingredients:
   6α,9α-difluoro-11β,17α-dihidroxy-16α-methyl-21-trimethyl-acetoxy-1,4-pregnadiene-3,20-dione;
   (+)-17,21-dipropionyloxy-16β-methyl-9α-fluoro-prednisolone;
   salicylic acid;
   tetracycline chloride;
   gentamycin sulfate;
   neomycin sulfate;
   trypsin; and
   chymotrypsin.

2. The composition of claim 1, further comprising a therapeutically effective amount of bismuth.

3. The composition of claim 1 in the form of a cream or an ointment.

4. The composition of claim 1 further comprising one or more adjuvants.

5. A composition useful for the treatment of psoriasis vulgaris, comprising
   about 6–12 mg. of 6α,9α-difluoro-11β,17α-dihidroxy-16α-methyl-21-trimethyl-acetoxy-1,4-pregnadiene-3,20-dione;
   about 20–25 mg. of (+)-17,21-dipropionyloxy-16β-methyl-9α-fluoro-prednisolone;
   about 3–10 g. of salicylic acid;
   about 9–14 g. of tetracycline chloride;
   at least about 45 mg. of gentamycin sulfate;
   about 200–250 mg. of neomycin sulfate;
   trypsin and chymotrypsin with a minimum enzymatic activity of 5,000 armour units each; and one or more inert adjuvants in a sufficient quantity to make 100 g. total.

6. The composition of claim 5 further comprising about 2–4 g. of bismuth.

7. A method for treating psoriasis vulgaris in humans, comprising topically applying a composition in accordance with claim 1, 5 or 6 in an effective amount to affected areas of the skin.

8. A method for the preparation of a pharmaceutical composition comprising:
   mixing 6α,9α-difluoro-11β,17α-dihidroxy-16βmethyl-21-trimethyl-acetoxy-1,4-pregnadiene-3,20dione with (+)-17,21-dipropionyloxy-16β-methyl-9α-fluoro-prednisolone at a temperature within the range of about 25°–30° C., and at a high relative humidity;
   allowing the composition to stand for 5–6 hours under the same conditions;
   lowering the temperature to about 5°–7° C. and lowering the humidity;
   adding salicylic acid, tetracycline chloride, gentamycin sulfate and neomycin sulfate;
   adding trypsin, chymotrypsin, and bismuth; and
   adding one or more inert adjuvants.

9. The method of claim 8 wherein the mixing of 6α,-9α-difluoro-11β,17α-dihidroxy-16α-methyl-21-trimethyl-acetoxy-1,4-pregnadiene with (+)-17,21-dipropionyloxy-16β-methyl-9α-fluoro-prednisolone occurs at a relative humidity of about 97% and an atmospheric pressure of about 980 millibars for about 10 minutes.

10. The method of claim 9 wherein the mixture of 6α,9α-difluoro-11β,17α-dihidroxy-16α-methyl-21-trimethyl-acetoxy-1,4-pregnadiene-3,20-dione and (+)-17,21-dipropionyloxy-16β-methyl-9α-fluoro-prednisolone is allowed to stand under the same conditions for about 5–6 hours.

11. The method of claim 10 wherein after the mixture has been allowed to stand for about 5–6 hours, the humidity is lowered to about 30% without changing the atmospheric pressure.

12. The method of claim 8 wherein salicylic acid, tetracycline chloride, gentamycin sufate and neomycin sulfate are added to the mixture containing 6α,9α-difluoro-11β,17α-dihidroxy-16α-methyl-21-trimethyl-acetoxy-1,4-pregnadiene-3,20-dione and (+)-17,21-dipropionyloxy-16β-methyl-9α-fluoro-prednisolone with intensive agitation for about 10–15 minutes.

13. The method of claim 12 wherein after the mixture is intensively agitated for 10–15 minutes, trypsin, chymotrypsin, and bismuth are added with additional mixing for about 5 minutes.

* * * * *